United States Patent
Hsung et al.

(10) Patent No.: US 10,716,930 B2
(45) Date of Patent: *Jul. 21, 2020

(54) CARDIAC PACEMAKER SYSTEM AND CONTROL METHOD THEREOF

(71) Applicant: SHANGHAI MICROPORT MEDICAL (GROUP) CO., LTD., Shanghai (CN)

(72) Inventors: Jean Cheui Hsung, Shanghai (CN); Guiling Li, Shanghai (CN); Min Huang, Shanghai (CN); Xinxin Chen, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 268 days.

This patent is subject to a terminal disclaimer.

(21) Appl. No.: 15/548,649

(22) PCT Filed: Jan. 8, 2016

(86) PCT No.: PCT/CN2016/070480
§ 371 (c)(1),
(2) Date: Aug. 3, 2017

(87) PCT Pub. No.: WO2016/124065
PCT Pub. Date: Aug. 11, 2016

(65) Prior Publication Data
US 2018/0015279 A1    Jan. 18, 2018

(30) Foreign Application Priority Data

Feb. 6, 2015  (CN) .......................... 2015 1 0063768

(51) Int. Cl.
*A61N 1/02*      (2006.01)
*A61N 1/36*      (2006.01)
(Continued)

(52) U.S. Cl.
CPC ............... *A61N 1/025* (2013.01); *A61N 1/36* (2013.01); *A61N 1/36507* (2013.01); *A61N 1/371* (2013.01); *A61N 1/37247* (2013.01)

(58) Field of Classification Search
CPC ...... A61N 1/025; A61N 1/36; A61N 1/36507; A61N 1/371; A61N 1/37247
See application file for complete search history.

(56) References Cited

U.S. PATENT DOCUMENTS

| | | | |
|---|---|---|---|
| 5,273,035 A | 12/1993 | Markowitz et al. | |
| 5,350,407 A * | 9/1994 | McClure | A61N 1/37252 607/16 |
| 5,716,384 A | 2/1998 | Snell | |

FOREIGN PATENT DOCUMENTS

| | | |
|---|---|---|
| CN | 203494059 U | 3/2014 |
| CN | 104606784 A | 5/2015 |

(Continued)

*Primary Examiner* — Catherine M Voorhees
*Assistant Examiner* — Roland Dinga
(74) *Attorney, Agent, or Firm* — Muncy, Geissler, Olds & Lowe, P.C.

(57) ABSTRACT

A cardiac pacemaker system and control methods thereof are disclosed, wherein pacing logic and timing functions are enabled by a microprocessor and sensing and pulse delivery capabilities are accomplished by a peripheral IC. The microprocessor communicates with the peripheral IC via serial interfaces and electrical level signals. This allows for full use of internal resources of the modern ultra-low power microprocessor, lowering the dependence of the system on the peripheral IC and reducing the effort required for digital circuit design.

20 Claims, 1 Drawing Sheet

(51) Int. Cl.
*A61N 1/37* (2006.01)
*A61N 1/365* (2006.01)
*A61N 1/372* (2006.01)

(56) References Cited

FOREIGN PATENT DOCUMENTS

| | | |
|---|---|---|
| CN | 104623804 A | 5/2015 |
| CN | 104623805 A | 5/2015 |
| CN | 104623809 A | 5/2015 |

* cited by examiner

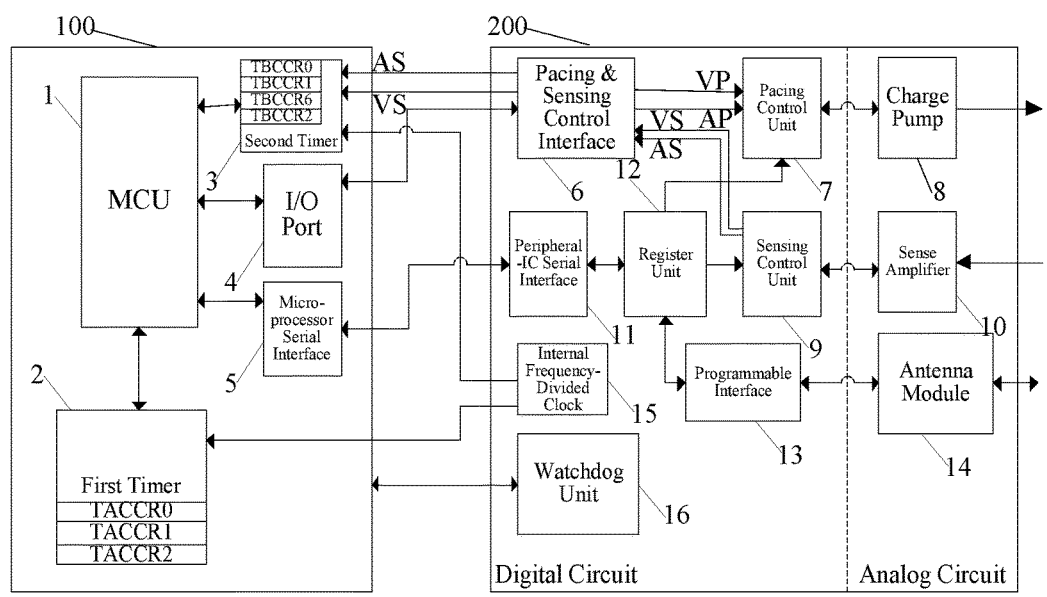

CARDIAC PACEMAKER SYSTEM AND CONTROL METHOD THEREOF

TECHNICAL FIELD

The present invention relates to the field of medical devices and, in particular, to a cardiac pacemaker system and control methods thereof.

BACKGROUND

A cardiac pacemaker is a medical device that can effectively treat cardiac arrhythmias by delivering pulse currents at a certain frequency to stimulate the heart to perform the blood-pumping function. The cardiac pacemaker employs a pulse generator to sense cardiac electrical signals and delivers pacing pulses as needed. For example, after the cardiac pacemaker senses an intrinsic atrial event via electrocardiogram (EGM) signal, the pulse generator sets an atrial sense refractory period and a lower rate limit and generates a pacing pulse at a proper time.

In the early ages, pacing control for cardiac pacemakers was performed by digital circuits incorporating pacing state machines. With the complexity of cardiac pacemaker functions increasing, cardiac pacemaker manufacturers added microprocessor cores to the digital circuits. The microprocessor cores were primarily responsible for data statistics and more sophisticated therapeutic functions while the logic control capabilities for the cardiac pacemaker functions are retained in the digital circuits.

In an existing cardiac pacemaker system, a digital circuit performs a great amount of pacemaker-related logic control, such as determining a variety of pacing modes including DDD, VVI, etc. This makes the performance of the cardiac pacemaker system highly hardware-dependent, which is not conducive to the expansion of functionality. In addition, reliability and verification of the digital circuit requires voluminous human and material resources and the system verification of the performance of the cardiac pacemaker system is thus not an easy task.

In another existing cardiac pacemaker system, pacing timing logics are provided by a microprocessor core and a supporting digital circuit. However, such a cardiac pacemaker system requires a great effort in the design of an application-specific integrated circuit (ASIC).

SUMMARY OF THE INVENTION

It is an objective of the present invention to provide a cardiac pacemaker system and control methods thereof, which solve the problem of requiring great effort in digital circuit design and verification by the existing cardiac pacemaker systems.

To this end, the present invention provides a cardiac pacemaker system including:

a microprocessor, including a main control unit, a first timer, a second timer, input/output ports and a microprocessor serial interface, wherein each of the first timer, the second timer, the input/output ports and the microprocessor serial interface is connected to the main control unit; and a peripheral IC, including a pacing and sensing control interface, a pacing control unit, a sensing control unit and a peripheral-IC serial interface, the pacing and sensing control interface being connected to each of the pacing control unit and the sensing control unit, wherein: the second timer and the input/output ports communicate with the pacing and sensing control interface by using a first electrical level signal and a second electrical level signal, respectively; the pacing and sensing control interface, upon sensing an atrial or ventricular event, notifies the second timer of the atrial or ventricular event by using the first electrical level signal; the input/output ports send a pacing request to the pacing and sensing control interface by using the second electrical level signal; the microprocessor serial interface is electrically connected to the peripheral-IC serial interface; and the microprocessor controls the peripheral IC to configure parameters by using data communicated between the serial interfaces.

Additionally, in the cardiac pacemaker system, when the main control unit is in a sleep state, the peripheral IC may wake up the main control unit through an interrupt upon detecting an electrocardiogram signal or detecting delivery of a pacing pulse, and wherein after the main control unit is woken up, the main control unit processes a current event without responding to any new interrupt until the main control unit completes processing of the current event.

Additionally, in the cardiac pacemaker system, the second timer may include a plurality of capture registers, wherein upon the peripheral IC detecting an electrocardiogram signal or detecting delivery of a pacing pulse, the peripheral IC notifies the second timer by using the first electrical level signal, the second timer captures the first electrical level signal indicative of the atrial or ventricular event, and the second timer records the actual time of occurrence of the atrial or ventricular event in one of the plurality of capture registers.

Additionally, the cardiac pacemaker system may further include a programming interface configured to communicate with a programmer, wherein: the cardiac pacemaker system combines information indicative of the atrial or ventricular event with information indicating the actual time of occurrence via the programming interface and sends the combined information to the programmer; the cardiac pacemaker system does not include a pacing mode program unit and the programmer sets a pacing mode defined by a user as a group of function control bits and sends values of the group of function control bits to the cardiac pacemaker system via the programming interface; and the cardiac pacemaker system performs pacing control based on the values of the group of function control bits.

Additionally, in the cardiac pacemaker system, the first timer may operate in an up-counting mode and the second timer may operate in a continuous mode, wherein: the first timer includes a first compare register, a second compare register and a third compare register, the first compare register operating in a comparing mode and being configured for control of escape interval, the second compare register operating in a comparing mode and being configured for control of an atrial/ventricular sense refractory period, the third compare register operating in a comparing mode and being configured for control of a post ventricular atrial sense refractory period;

the second timer includes a fourth capture register, a fifth capture register, a sixth capture register and a seventh compare register, the fourth capture register operating in a capture mode and being configured for recording the delivery time of a pacing pulse, the fifth capture register operating in a capture mode and being configured for recording the actual atrial sense time, the sixth capture register operating in a capture mode and being configured for recording the actual ventricular sense time, the seventh compare register operating in a comparing mode to provide a clock system for the cardiac pacemaker system.

Additionally, in the cardiac pacemaker system, the peripheral IC may include a digital circuit including the pacing and sensing control interface, the pacing control unit, the sensing control unit, the peripheral-IC serial interface, a registers set, a programming interface and an internal frequency-divided clock unit, the registers set electrically connected to each of the pacing control unit, the peripheral-IC serial interface, the sensing control unit and the programming interface, the internal frequency-divided clock unit electrically connected to each of the first timer and the second timer.

Additionally, in the cardiac pacemaker system, the peripheral IC may include an analog circuit including a charge pump, sense amplifiers and an antenna module, the charge pump connected to the pacing control unit, the sense amplifiers connected to the sensing control unit, the antenna module connected to the programming interface.

A control method of a cardiac pacemaker system for controlling the cardiac pacemaker system defined above includes:

upon detection of an electrocardiogram signal or delivery of a pacing pulse by the peripheral IC, notifying the microprocessor of an atrial or ventricular event by using the first electrical level signal, capturing the first electrical level signal indicative of the atrial or ventricular event by the second timer, and recording an actual time of occurrence of the atrial or ventricular event in one of the plurality of capture registers of the second timer so that the actual time of occurrence of the atrial or ventricular event is recorded;

when the microprocessor captures the atrial or ventricular event, setting a next cardiac chamber to be paced based on a current pacing mode and calculating a time for the next cardiac chamber to be paced and storing the time for the next cardiac chamber to be paced in a compare register of the first timer, by the microprocessor, and when a value of the first timer becomes equal to a value of the compare register, sending a request for pacing of the next cardiac chamber to the peripheral IC by using the second electrical level signal, by the microprocessor; and notifying the microprocessor of the delivery of the pacing pulse as another atrial or ventricular event, by the peripheral IC.

Additionally, in the control method, when the main control unit is in a sleep state, the peripheral IC may wake up the main control unit through an interrupt upon detecting the electrocardiogram signal or detecting delivery of the pacing pulse, and wherein after the main control unit is woken up, the main control unit processes a current event without responding to any new interrupt until the main control unit completes processing of the current event.

Additionally, the control method may further include: transmitting the pacing mode set in the programmer as well as parameters associated with the pacing mode to the peripheral IC via the programming interface and storing the parameters in a registers set of the peripheral IC via the programming interface; reading, by the microprocessor, the parameters in the registers set via the microprocessor serial interface; and displaying the pacing mode and operating parameters of the cardiac pacemaker on a user interface of the programmer.

Additionally, the control method may further include: setting the pacing mode defined by a user as a group of function control bits; sending values of the group of function control bits to the cardiac pacemaker system via the programming interface; and performing pacing control by the cardiac pacemaker system based on the values of the group of function control bits.

Additionally, in the control method, the group of function control bits may be a group of bits.

The cardiac pacemaker system and its control methods according to the present invention provide the following benefits: the pacing logic and timing functions are performed by firmware in the microprocessor, while the sensing and pulse delivery capabilities are accomplished by the peripheral IC. This allows for full use of internal resources of the modern ultra-low power microprocessor, lowering the dependence of the system on the peripheral IC and reducing the effort required for digital circuit design.

BRIEF DESCRIPTION OF THE DRAWINGS

The sole FIGURE is a diagram schematically illustrating a cardiac pacemaker system and its control methods according to embodiments of the present invention.

DETAILED DESCRIPTION

The cardiac pacemaker system and its control methods of the present invention will be described in greater detail below with reference to the accompanying drawing as well as to particular embodiments. The features and advantages of the invention will be more apparent from the following detailed description, as well as from the appended claims. It is noted that the accompanying drawings are provided in a very simplified form not necessarily presented to scale, with the only purpose of facilitating convenience and clarity in explaining the embodiments.

Referring to the sole FIGURE, the present invention provides a cardiac pacemaker system including a microprocessor 100 and a peripheral integrated circuit (IC) 200, wherein the microprocessor 100 is able to communicate with the peripheral IC 200. According to the present invention, the pacing logic and timing functions are performed by firmware in the microprocessor 100, while the sensing and pulse delivery capabilities are accomplished by the peripheral IC 200. This allows for full use of internal resources of the modern ultra-low power, microprocessor 100 lowering the dependence of the system on the peripheral IC 200 and reducing the effort required for digital circuit design.

Connections between and the various components capabilities thereof according to the present invention will be explained in detail below.

As shown in the sole FIGURE, the microprocessor 100 includes a main control unit (MCU) 1, a first timer 2 (TA timer), a second timer 3 (TB timer), an input/output (I/O) port 4 and a microprocessor serial interface 5. Each of the first timer 2, the second timer 3, the I/O port 4 and the microprocessor serial interface 5 is connected to the MCU 1. The MCU 1 is adapted to perform various functionality-related control including pacing timing control and IC parameter configuration. The first timer 2 includes three registers and the second timer 3 includes six registers, which are configured for timing and real-time recording of electrocardiogram (EGM) events or actual delivery time of pacing pulses. The I/O port 4 is configured to deliver high and low levels for pacing control of the peripheral IC 200, and the microprocessor serial interface 5 is provided to enable data communication between the MCU 1 and a digital circuit in the peripheral IC 200.

The peripheral IC 200 includes a digital circuit and an analog circuit. The digital circuit includes a pacing and sensing control interface 6, a pacing control unit 7, a sensing control unit 9, a peripheral-IC serial interface 11, a registers set 12, a programming interface 13, an internal frequency-divided clock unit 15 and a watchdog unit 16. The analog circuit includes a charge pump 8, a sense amplifier 10 and an antenna module 14.

The pacing and sensing control interface 6 is electrically connected to each of the second timer 3, the I/O port 4, the pacing control unit 7 and the sensing control unit 9. The registers set 12 is connected to each of the pacing control unit 7, the peripheral-IC serial interface 11, the sensing control unit 9 and the programming interface 13. The peripheral-IC serial interface 11 is further connected to the microprocessor serial interface 5. The internal frequency-divided clock unit 15 is connected to both the first timer 2 and the second timer 3, and the watchdog unit 16 is connected to the microprocessor 100. The charge pump 8 is connected to the pacing control unit 7, the sense amplifier 10 is connected to the sensing control unit 9 and the antenna module 14 is connected to the programming interface 13.

In the embodiment, upon the occurrence of an atrial or ventricular event, the sense amplifier 10 receives an analog EGM signal in real time and transfers the analog EGM signal to the sensing control unit 9. The sensing control unit 9 checks the effectiveness of the EGM signal and generates an atrial sense (AS) signal or a ventricular sense (VS) signal based on the EGM signal. It further sends the AS or VS signal to the pacing and sensing control interface 6, and the pacing and sensing control interface 6 passes the AS or VS signal to the second timer through a first electrical connection line. Upon receiving the AS or VS signal, the second timer records the actual time of occurrence (TOC) of the EGM event to which the signal corresponds in its internal register based on the timer's timing clock.

The MCU 1 is normally in a sleep state. Upon the receipt of the AS or VS signal, the second timer wakes up the MCU 1 so that the MCU 1 executes a corresponding interrupt service routine. The MCU 1 determines the next cardiac chamber to be paced and the time for pacing the next cardiac chamber based on the current pacing mode and sets them in a compare register of the first timer that functions as an escape control means. When a value of the first timer becomes equal to a value of the compare register, the MCU 1 sends a corresponding pacing request through a second electrical connection line to the pacing and sensing control interface 6 via the I/O port 4 and sets the cardiac chamber to be paced. The pacing and sensing control interface 6 decodes the pacing request and transmits an atrial pacing (AP) signal or a ventricular pacing (VP) signal to the pacing control unit 7.

The pacing control unit 7 is further adapted to control and monitor the circuit operation of the charge pump 8, and the charge pump 8 enables charge control of the pacing circuit. The internal frequency-divided clock unit 15 is connected to both the first timer 2 and the second timer 3 so as to provide a timing base to the first timer 2 and the second timer 3 with a resolution of 1 msec. During the pacing, the sensing control unit 9 carries out control such that the sense amplifier 10 is turned on or off. The registers set 12 is provided to store data of the sensing control unit 9, the pacing control unit 7, the programming interface 13 and the antenna module 14, which can be read by a programmer via the microprocessor 100. Data communication can be conducted between the peripheral-IC serial interface 11 and the microprocessor serial interface 5. The programming interface 13 is responsible for reception and check of program data, generation of corresponding interrupts and transmission of data in accordance with protocols. The antenna module 14 converts analog antenna signals to digital signals. The watchdog unit 16 monitors the operation of the system to prevent the occurrence of crashes and program errors.

Operating modes of the timers will be described below in greater detail below.

The first timer 2 operates in an up-counting mode. The first timer 2 includes a TACCR0 (first compare register) which operates in an up-counting mode for escape control. After a pacing or sensing event, the MCU 1 sets an escape interval for the next pacing in the first compare register. As the first timer 2 operates in the up-counting mode, it counts up from 0 until the escape interval expires, i.e., the value of the first timer becomes equal to the value set in the first compare register. Then it generates an interrupt, and the MCU 1 sends a pacing request to the pacing circuit. The first timer 2 further includes: a TACCR1 (second compare register) which operates in a comparing mode and is configured for control of an atrial/ventricular sense refractory period; and a TACCR2 (third compare register) which operates in a comparing mode and is configured for control of a post ventricular atrial sense refractory period. The so-called refractory period control refers to, during resetting of the sense refractory periods, setting corresponding VRP and PVARP bits of a pacing control variable (pc_ctrl) apart from setting values of the sense refractory periods in TACCR1 and TACCR2. When the refractory period expires, a corresponding bit is set to "0", and it is determined whether the event is a sense event that occurred during the refractory period through checking a corresponding control bit.

The second timer 3 operates in a continuous mode. The second timer 3 includes: a TBCCR0 (fourth capture register) that operates in a capture mode and is configured for recording of pacing pulse delivery time; a TBCCR1 (fifth capture register) that operates in a capture mode and is configured for recording of atrial sense time; a TBCCR6 (sixth capture register) that operates in a capture mode and is configured for recording of ventricular sense time; a TBCCR2 (seventh compare register) that operates in a comparing mode and generates an interrupt in every second. A clock system for the whole system is established based on such one-second interrupts. In the interrupt service routine, four bytes are used as a time counter that can increment by one after every second for a total of 136 years. This interrupt service routine can also provide service for some timing request (with a resolution of one second or more). In this embodiment, the second timer 3 can further include an eighth compare register, a ninth compare register and a tenth compare register (not shown). The eighth compare register operates in a comparing mode and is configured to generate an interrupt lasting for a period of time in the resolution of milliseconds. The ninth and tenth compare registers are both operate in a comparing mode and are configured to generate events for test scenarios usable in verification testing of the MCU 1.

Depending on the type of the events, the atrial sense time, ventricular sense time and time of occurrence of the pacing event are frozen in the capture registers of the second timer 3. Therefore, the calculation of the next escape interval is immunized from delays in real-time response of the firmware to the interrupts. Atrial sense, ventricular sense and pacing interrupt service routines put the TOCs and forms of the events in a circular buffer so that they can serve as a basis for the calculation of the next pacing time.

Further, in the pacemaker, all pacing actions are under the control of a pacing control variable pc_ctrl and all subsequent actions are determined based on the values of bits in the variable.

Definitions of these pacing bits are summarized in the following Table 1 and are explained in detail as follows:
Bit 1: 1, during a VRP period; otherwise, 0
Bit 2: 1, during a PVARP period; otherwise, 0
Bit 3: 1, during a PANP period; otherwise, 0
Bit 4: PVC event
Bit 5: Multi-PVC event
Bit 6: Cardiac chamber: 1: V, 0: A
Bit 7: Triggered pacing
Bit 8: Set to indicate the occurrence of a previous A event
Bit 9: Set to indicate the occurrence of a previous V event
Bit 10: Set during an Inhibit period
Bit 11: Set during a PMT
Bit 12: Reserve

TABLE 1

| 7 | 6 | 5 | 4 | 3 | 2 | 1 | 0 |
|---|---|---|---|---|---|---|---|
| PC_CTRL_ TGM | PC_CTRL_ CHAMBER_V | PC_CTRL_ RPVC | PC_CTRL_ PVC | PC_CTRL_ PANP | PC_CTRL_ PVARP | PC_CTRL_ VRP | PC_CTRL_ ARP |
| 15 | 14 | 13 | 12 | 11 | 10 | 9 | 8 |
|  |  |  | PC_CTRL_ NM | PC_CTRL_ PMTNI | PC_CTRL_ INHIB | PC_CTRL_ VINT | PC_CTRL_ AINT |

Preferably, in the present invention, a programming of parameters is completed in one program-controlled wake-up service routine. Such parameters are categorized into two sets.

One set is stored in a memory of the MCU 1 so that the parameters can be read and written by the MCU directly. This set of parameters has two backups which can be entirely validated at regular intervals. If one backup fails in validation, it can be restored based on the other backup. If the validation of both backup fails, the parameters can be reverted to factory default settings using data stored on a flash memory.

The other set is stored in the registers set 12 of the peripheral IC, and read/write operations about the parameters therein must be done via the serial interfaces. Since modifications to the peripheral IC often involve modifying the bits, in order to dispense with the need to exchange two bytes between the serial interfaces for the modification of any bit (or any combination of bits), one copy of the registers set is kept in a memory and another copy thereof is reserved in the programmer. Further, the memory may keep two copies of the registers set. The validation and restoration of these parameters is similar to those in the first set. Such regular checks can prevent errors in uniformity across the memories.

Further, it is preferable that interrupts are only enabled when the MCU 1 is in the sleep state. As such, upon the occurrence of an event, such as atrial sense, ventricular sense, programming or expire of the first or second timer 2 or 3, the MCU 1 will be woken up and enter the interrupt service routine for related processing. Once the MCU 1 has been awakened, global interrupts are disabled (but interrupts that have occurred will not be lost) during operation of the MCU that lasts for several milliseconds (up to 3-6 ms). Follows the completion of the current interrupt service routine, the pending interrupt in the sequence will be handled according to their priority. In this embodiment, since nested interrupts are not allowed, the system behaves in a deterministic fashion. This design simplifies not only the processing of programming and other asynchronous events and cardiac events but also the verification of pacing performance, in particular the system behavior related to the propriety of pacing timing.

Accordingly, the present invention also provides a control method of a cardiac pacemaker system that uses the cardiac pacemaker system as discussed above, including the steps detailed below.

In Step 1, when the peripheral IC detects a cardiac event via EGM signal or detects delivery of a pacing pulse, it notifies microprocessor of an atrial or ventricular event by changing a voltage level on the first electrical connection line. The second timer then captures the first electrical level signal that represents the atrial or ventricular event and records the actual TOC of the atrial or ventricular event in a capture register of the second timer so that the time of occurrence of the atrial or ventricular event is recorded.

The microprocessor is normally in the sleep state and will be woken up by an interrupt upon the detection of the EGM signal or delivery of the pacing pulse. After the microprocessor is woken up, the MCU processes the current event without responding to any new interrupt until it completes the processing of the current event.

In Step 2, when the microprocessor captures the atrial or ventricular event, it sets the next cardiac chamber to be paced based on the current pacing mode and calculating the time for the next pacing. These parameters are then configured in a compare register of the first timer. When a value of the first timer becomes equal to a value of the compare register, the microprocessor sends a request for pacing of the next cardiac chamber to the peripheral IC by changing a voltage level on the second electrical connection line.

In Step 3, the peripheral IC notifies the microprocessor of the delivery of the pacing pulse as another atrial or ventricular event.

In addition, the cardiac pacemaker system may be further provided with an external programmer which can conduct wireless communication with the system. Similarly, the atrial sense, ventricular sense and pacing interrupt service routines concentrate the TOCs and forms of the events into two bytes as time-stamped markers and upload them to the programmer. Unlike traditional ones, these markers uploaded to the programmer are associated with time information based on the pacemaker's time scheme. Based on these time-stamped markers, the programmer can provide the user with more accurate data on the intervals in real time. The time-stamped markers can also provide a powerful tool for system verification and testing. The programmer is equipped with a user interface which allows adjustments in parameters of the implanted medical device. For example, the microprocessor may wirelessly transfer settings for pacing amplitude and sense threshold to the register unit in the digital module of the peripheral IC via the serial interfaces.

Accordingly, another control method of the cardiac pacemaker system is also provided, including the steps of:

transmitting, by the external programmer, a pacing mode and associated parameters to the peripheral IC of the cardiac pacemaker system via the programming interface and storing the parameters in the registers set unit of the peripheral IC via the programming interface; reading, by the microprocessor, the parameters in the registers set unit through the microprocessor serial interface; and adjusting the operating mode and parameters of the cardiac pacemaker on the user interface of the programmer.

Further, the associated parameters with the pacing mode may include a lower rate limit and/or an upper tracking rate limit.

Further, the parameters of the medical device may include a pacing amplitude and/or a sense threshold.

Further, the pacing mode may realize inputs on the user interface of the external programmer by virtue of AAI, VVI or DDD. An application of the external programmer may convert the pacing mode into a group of bits, and the microprocessor may subsequently perform logic processing on a system behavior corresponding to the pacing mode based on the converted set of bits. In particular, as there is no direct control over sensing switches of the peripheral IC, atrial and ventricular sensing is enabled no matter the mode is AAI, VVI or DDD.

The conversion of the pacing mode to the bit group is further illustrated with reference to the following Table 2.

TABLE 2

|     | 7 NM | 6 DAV | 5 I/T | 4 VP | 3 AP | 2 DS | 1 VS | 0 AS |
|-----|------|-------|-------|------|------|------|------|------|
| AAI | 0 | 0 | 0 | 0 | 1 | 0 | 0 | 1 |
| AAT | 0 | 0 | 1 | 0 | 1 | 0 | 0 | 1 |
| AOO | 0 | 0 | 0 | 0 | 1 | 0 | 0 | 0 |
| OAO | 0 | 0 | 0 | 0 | 0 | 0 | 0 | 1 |
| VVI | 0 | 0 | 0 | 1 | 0 | 0 | 1 | 0 |
| VVT | 0 | 0 | 1 | 1 | 0 | 0 | 1 | 0 |
| VOO | 0 | 0 | 0 | 1 | 0 | 0 | 0 | 0 |
| OVO | 0 | 0 | 0 | 0 | 0 | 0 | 1 | 0 |
| DDD | 0 | 0 | 1 | 1 | 1 | 1 | 1 | 1 |
| DDI | 0 | 0 | 0 | 1 | 1 | 1 | 1 | 1 |

The cardiac pacemaker system and control methods thereof according to the present invention offer the following advantages:

Firstly, the control of pacing amplitude, pulse width and sensing sensitivity, etc. is accomplished using a group of registers in the peripheral IC developed by the present invention. The MCU and the peripheral IC communicate with each other via the serial peripheral interfaces (SPIs). There is no need for logic control of cardiac chamber pacing and timing to write the ASIC register group, just only when modifications to the pacing amplitude, pulse width, sensing sensitivity control, etc. Write operations on the ASIC register group are made by the user. In addition, the read/write operations on the ASIC registers are completed in one time after the MCU is woken up by a telemetry program.

Secondly, the cardiac pacemaker system of the present invention is capable of sensing the TOC of pacing (with an accuracy of one millisecond), and the time for the next pacing can be calculated by the interrupt service routine which can obtain the current time information by reading the TB counter TBR before it configures the escape interval in the TACCR0. Therefore, control granularity for pacing interval can be as fine as within 2 milliseconds.

Thirdly, as communication between the microprocessor and the peripheral hardware, for example, for read/write operations on the registers in the digital circuit, is carried out via the serial interfaces. If all tasks related to pacing control were fulfilled in such a way, there would be a waste of time and effort. According to the present invention, read/write operations on the hardware registers are only required for interactions with the programmer, for example, for configuration of the pacing amplitude, pulse width, etc., while control of pacing timing with a granularity of several minutes, seconds or milliseconds, such as selection of the pacing of the cardiac chamber or the request for pacing by the hardware, is accomplished by configuration of a high/low level via the I/O port.

The foregoing description presents merely a few preferred embodiments of the present invention and does not limit the scope thereof in any sense. All changes or modifications made in light of the above disclosure by any person of ordinary skill in the art fall within the scope of protection set forth in the appended claims.

The invention claimed is:

1. A cardiac pacemaker system, comprising:
a microprocessor, comprising a main control unit, a first timer, a second timer, input/output ports and a microprocessor serial interface, wherein each of the first timer, the second timer, the input/output ports and the microprocessor serial interface is connected to the main control unit; and
a peripheral IC, comprising a pacing and sensing control interface, a pacing control unit, a sensing control unit and a peripheral-IC serial interface, the pacing and sensing control interface being connected to each of the pacing control unit and the sensing control unit,
wherein: the second timer and the input/output ports communicate with the pacing and sensing control interface by using a first electrical level signal and a second electrical level signal, respectively; the pacing and sensing control interface, upon sensing an atrial or ventricular event, notifies the second timer of the atrial or ventricular event by using the first electrical level signal; the input/output ports send a pacing request to the pacing and sensing control interface by using the second electrical level signal; the microprocessor serial interface is electrically connected to the peripheral-IC serial interface; and the microprocessor controls the peripheral IC to configure parameters by using data communicated between the serial interfaces.

2. The cardiac pacemaker system of claim 1, wherein when the main control unit is in a sleep state, the peripheral IC wakes up the main control unit through an interrupt upon detecting the atrial or ventricular event via an electrocardiogram signal or detecting delivery of a pacing pulse, and wherein after the main control unit is woken up, the main control unit processes a current event without responding to any new interrupt until the main control unit completes processing of the current event.

3. The cardiac pacemaker system of claim 1, wherein the second timer comprises a plurality of capture registers, wherein upon the peripheral IC detecting an electrocardiogram signal or detecting delivery of a pacing pulse, the peripheral IC notifies the second timer by using the first electrical level signal, the second timer captures the first electrical level signal indicative of the atrial or ventricular event, the first electrical level signal corresponding to an actual time of occurrence of the atrial or ventricular event, and the second timer records the actual time of occurrence of the atrial or ventricular event in one of the plurality of capture registers.

4. The cardiac pacemaker system of claim 3, wherein: the peripheral IC further comprises a programming interface configured to communicate with a programmer; the cardiac pacemaker system combines information indicative of the atrial or ventricular event with information indicating the actual time of occurrence via the programming interface and sends the combined information to the programmer.

5. The cardiac pacemaker system of claim 1, wherein the first timer operates in an up-counting mode,
wherein: the first timer comprises a first compare register, a second compare register and a third compare register, the first compare register operating in a comparing mode and being configured for control of escape interval, the second compare register operating in a comparing mode and being configured for control of an atrial/ventricular sense refractory period, the third compare register operating in a comparing mode and being configured for control of a post ventricular atrial sense refractory period.

6. The cardiac pacemaker system of claim 1, wherein the peripheral IC comprises a digital circuit comprising the pacing and sensing control interface, the pacing control unit, the sensing control unit, the peripheral-IC serial interface, a registers set, a programming interface and an internal frequency-divided clock unit, the registers set electrically connected to each of the pacing control unit, the peripheral-IC serial interface, the sensing control unit and the programming interface, the internal frequency-divided clock unit electrically connected to each of the first timer and the second timer.

7. The cardiac pacemaker system of claim 6, wherein the peripheral IC comprises an analog circuit comprising a charge pump, sense amplifiers and an antenna module, the charge pump connected to the pacing control unit, the sense amplifiers connected to the sensing control unit, the antenna module connected to a programming interface.

8. A control method of a cardiac pacemaker system for controlling the cardiac pacemaker system of claim 6, comprising:
transmitting the pacing mode set in the programmer as well as parameters associated with the pacing mode to the peripheral IC via the programming interface and storing the parameters in a registers set of the peripheral IC via the programming interface; reading, by the microprocessor, the parameters in the registers set via the microprocessor serial interface; and displaying the pacing mode and operating parameters of the cardiac pacemaker on a user interface of the programmer.

9. The control method of a cardiac pacemaker system of claim 8, further comprising: setting the pacing mode defined by a user as a group of function control bits;
sending values of the group of function control bits to the cardiac pacemaker system via the programming interface; and performing pacing control by the cardiac pacemaker system based on the values of the group of function control bits.

10. The control method of a cardiac pacemaker system of claim 8, wherein the group of function control bits is a group of bits.

11. The cardiac pacemaker system of claim 6, wherein a pacing mode set in a programmer as well as parameters associated with the pacing mode are transmitted to the peripheral IC via the programming interface and the parameters are stored in a registers set of the peripheral IC via the programming interface, and the microprocessor reads the parameters in the registers set via the microprocessor serial interface.

12. A control method of a cardiac pacemaker system for controlling the cardiac pacemaker system of claim 1, comprising:
upon detection of an electrocardiogram signal or delivery of a pacing pulse by the peripheral IC, notifying the microprocessor of an atrial or ventricular event by using the first electrical level signal, capturing the first electrical level signal indicative of the atrial or ventricular event by the second timer, and recording an actual time of occurrence of the atrial or ventricular event in one of the plurality of capture registers of the second timer so that the actual time of occurrence of the atrial or ventricular event is recorded.

13. The control method of a cardiac pacemaker system of claim 12, wherein when the main control unit is in a sleep state, the peripheral IC wakes up the main control unit through an interrupt upon detecting the electrocardiogram signal or detecting delivery of the pacing pulse, and wherein after the main control unit is woken up, the main control unit processes a current event without responding to any new interrupt until the main control unit completes processing of the current event.

14. The control method of a cardiac pacemaker system of claim 12, wherein when the microprocessor captures the atrial or ventricular event, setting a next cardiac chamber to be paced based on a current pacing mode and calculating a time for the next cardiac chamber to be paced and storing the time for the next cardiac chamber to be paced in a compare register of the first timer, by the microprocessor, and when a value of the first timer becomes equal to a value of the compare register, sending a request for pacing of the next cardiac chamber to the peripheral IC by using the second electrical level signal, by the microprocessor; and
notifying the microprocessor of the delivery of the pacing pulse as another atrial or ventricular event, by the peripheral IC.

15. The cardiac pacemaker system of claim 1, wherein when the microprocessor captures the atrial or ventricular event, setting a next cardiac chamber to be paced based on a current pacing mode and calculating a time for the next cardiac chamber to be paced and storing the time for the next cardiac chamber to be paced in a compare register of the first timer, by the microprocessor, and when a value of the first timer becomes equal to a value of the compare register, sending a request for pacing of the next cardiac chamber to the peripheral IC by using the second electrical level signal, by the microprocessor.

16. The cardiac pacemaker system of claim 1, wherein the peripheral IC notifies the microprocessor of delivery of a pacing pulse as another atrial or ventricular event.

17. The cardiac pacemaker system of claim 1, wherein a pacing mode is set as a group of function control bits, and the cardiac pacemaker system performs a pacing control based on values of the group of function control bits.

18. The cardiac pacemaker system of claim 17, wherein the group of function control bits is a group of bits.

19. The cardiac pacemaker system of claim 17, wherein the peripheral IC further comprises a programming interface configured to communicate with a programmer, the values of the group of function control bits are sent to the cardiac pacemaker system via the programming interface.

20. The cardiac pacemaker system of claim 1, wherein the second timer operates in a continuous mode,
wherein: the second timer comprises a fourth capture register, a fifth capture register, a sixth capture register and a seventh compare register, the fourth capture register operating in a capture mode and being configured for recording of delivery time of a pacing pulse, the fifth capture register operating in a capture mode and being configured for recording of actual atrial sense time, the sixth capture register operating in a capture mode and being configured for recording of actual ventricular sense time, the seventh compare register operating in a comparing mode and configured to generate an interrupt and provide a clock system for the cardiac pacemaker system.

* * * * *